United States Patent
Cattaneo et al.

(10) Patent No.: US 8,419,674 B2
(45) Date of Patent: Apr. 16, 2013

(54) INTRAVENOUS OXYGENATOR WITH IMPERMEABLE SHEATH AND WIRE GRATE

(75) Inventors: Giorgio Cattaneo, Aachen (DE); Helmut Reul, Düren (DE); Sylvia Ruth Reul-Freudenstein, legal representative, Düren (DE); Michele Lenz, legal representative, Frankfurt (DE); Jan Reul, legal representative, Düren (DE); Julian Paul Reul, legal representative, Düren (DE); Rüdiger Autschbach, Aachen (DE)

(73) Assignee: Novalung GmbH, Hechingen (DE)

( * ) Notice: Subject to any disclaimer, the term of this patent is extended or adjusted under 35 U.S.C. 154(b) by 899 days.

(21) Appl. No.: 12/384,541

(22) Filed: Apr. 6, 2009

(65) Prior Publication Data
US 2009/0254022 A1    Oct. 8, 2009

Related U.S. Application Data

(62) Division of application No. 10/522,331, filed as application No. PCT/DE03/02455 on Jul. 22, 2003, now Pat. No. 7,641,853.

(30) Foreign Application Priority Data

Jul. 22, 2002  (DE) ................. 102 33 290
Oct. 11, 2002  (DE) ................. 102 47 629

(51) Int. Cl.
    *A61M 37/00*    (2006.01)
(52) U.S. Cl.
    USPC ........................................................ 604/23
(58) Field of Classification Search ............ 604/6.14, 604/23, 26
    See application file for complete search history.

(56) References Cited

U.S. PATENT DOCUMENTS

| 4,583,969 A | 4/1986 | Mortensen et al. |
| 4,631,053 A | 12/1986 | Taheri |

(Continued)

FOREIGN PATENT DOCUMENTS

| DE | 90 02 100 | 7/1990 |
| EP | 0 507 724 | 10/1992 |

(Continued)

OTHER PUBLICATIONS

Notification Of Reasons For Refusal in English of Japanese Office Action dated Feb. 9, 2010.

(Continued)

*Primary Examiner* — Kevin C Sirmons
*Assistant Examiner* — Bradley Osinski
(74) *Attorney, Agent, or Firm* — Collard & Roe, P.C.

(57) ABSTRACT

An intravenous oxygenator for enriching blood with oxygen, said oxygenator having a bundle of fibers, said fibers being each connected to a gas supply means through a first connection and to a gas evacuation means through a second connection, with the fiber bundle being twisted during operation by relative rotation of the first connections of the fibers relative to the second connections of the fibers about a longitudinal axis of the oxygenator. Further, an intravenous oxygenator for insertion into a vein, the connections being respectively connected to a first and to a second fiber holder and being displaceable along a longitudinal axis of the oxygenator, with the fiber holders being mounted so as to be rotatable relative to one another about the longitudinal axis of the oxygenator. Such a constellation permits particularly efficient gas exchange.

19 Claims, 9 Drawing Sheets

U.S. PATENT DOCUMENTS

Figure 1:
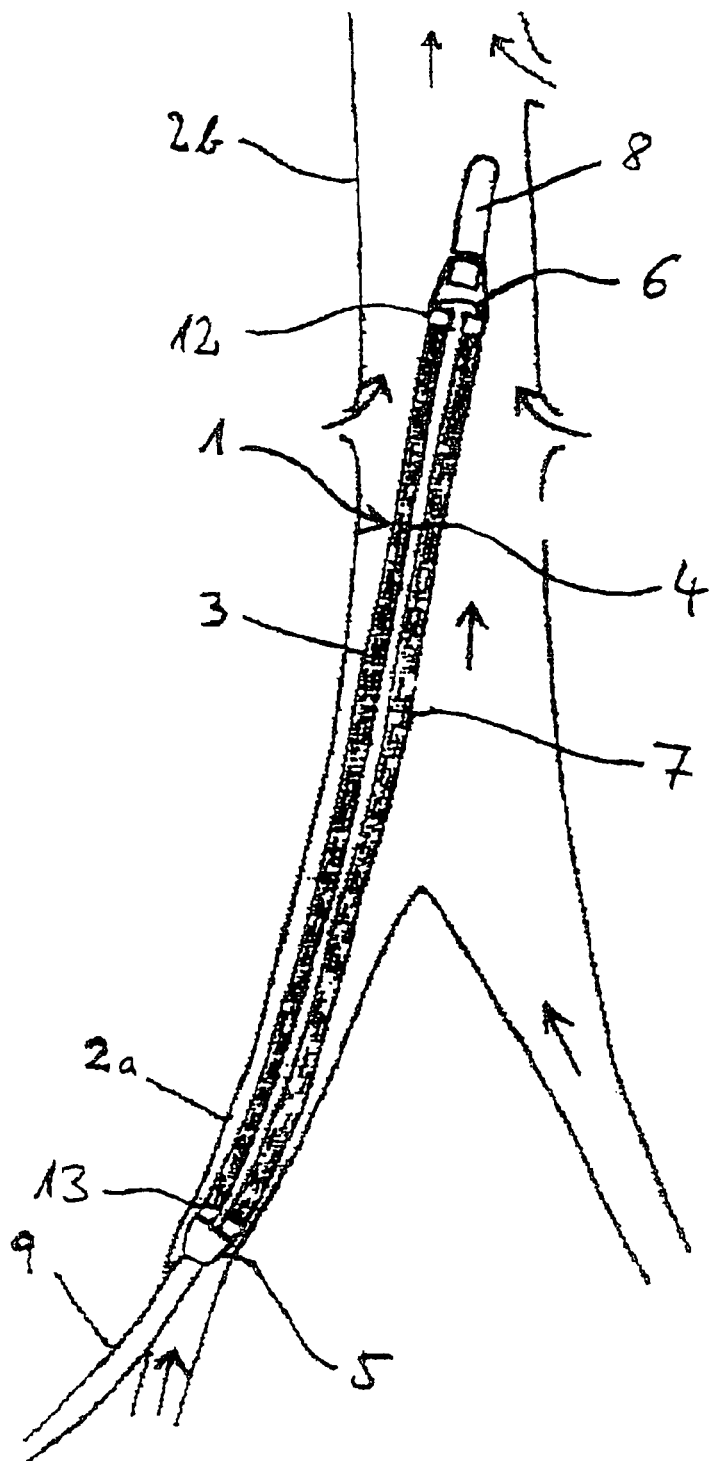

| | | | |
|---|---|---|---|
| 4,850,958 A | | 7/1989 | Berry et al. |
| 4,911,689 A | | 3/1990 | Hattler |
| 4,986,809 A | * | 1/1991 | Hattler ............................. 604/26 |
| 5,037,383 A | * | 8/1991 | Vaslef et al. .................... 604/26 |
| 5,098,376 A | | 3/1992 | Berry et al. |
| 5,125,902 A | | 6/1992 | Berry et al. |
| 5,219,326 A | * | 6/1993 | Hattler ............................ 604/26 |
| 5,487,727 A | | 1/1996 | Snider et al. |
| 5,501,663 A | * | 3/1996 | Hattler et al. ................... 604/26 |
| 5,814,011 A | | 9/1998 | Corace |

FOREIGN PATENT DOCUMENTS

| | | |
|---|---|---|
| EP | 0 631 790 | 1/1995 |
| JP | 5-501216 | 3/1993 |
| JP | H05-501216 | 3/1993 |
| JP | 06-053165 | 2/1994 |
| JP | H06-022618 | 3/1994 |
| JP | H06-053165 | 7/1994 |
| JP | 2001-070442 | 3/2001 |
| WO | WO 91/09642 | 7/1991 |
| WO | WO 97 39785 | 10/1997 |
| WO | WO 97/39785 | 10/1997 |
| WO | WO 02 076530 | 10/2002 |

OTHER PUBLICATIONS

Notification Of Reasons For Refusal in English.
International Search Report.
European Search Report.
English translation of International Preliminary Examination Report.

* cited by examiner

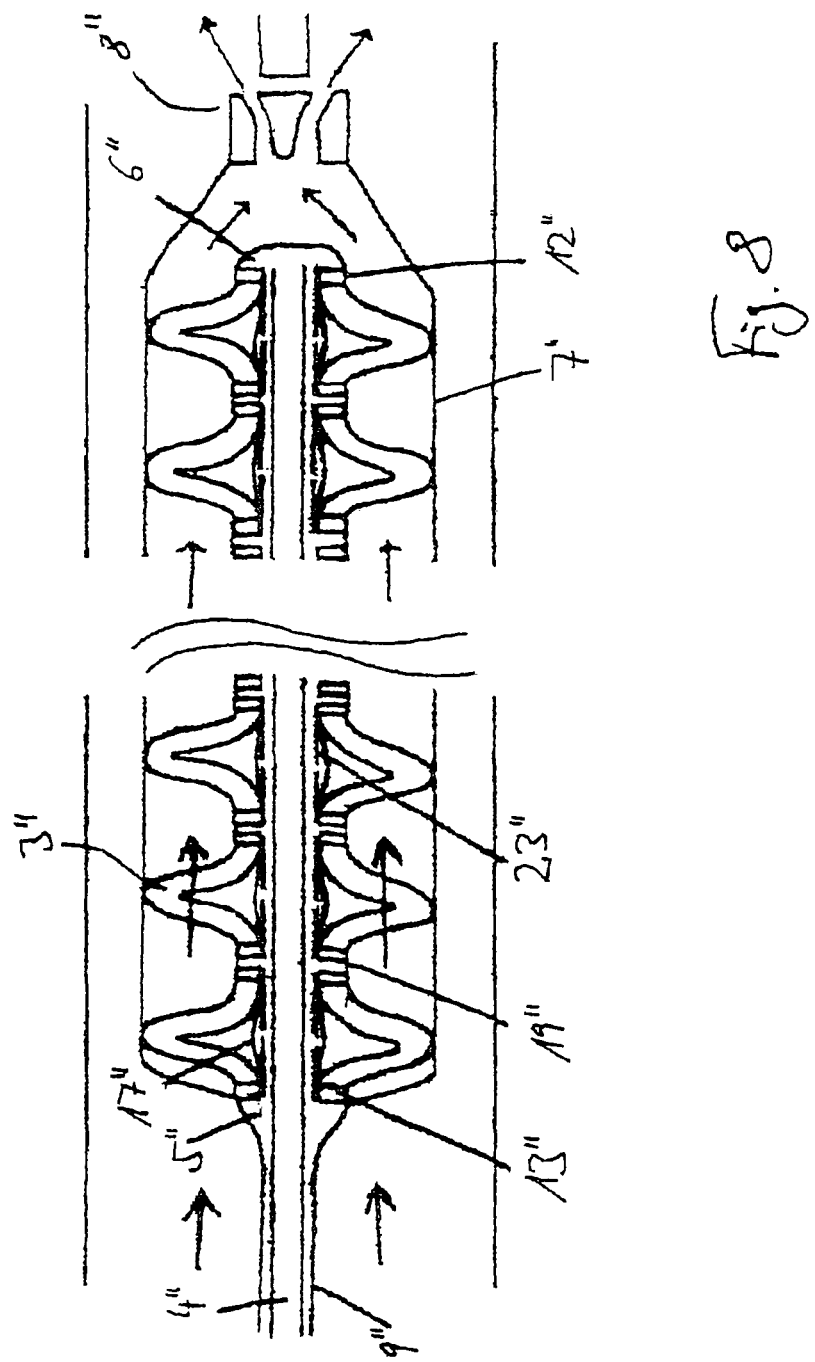

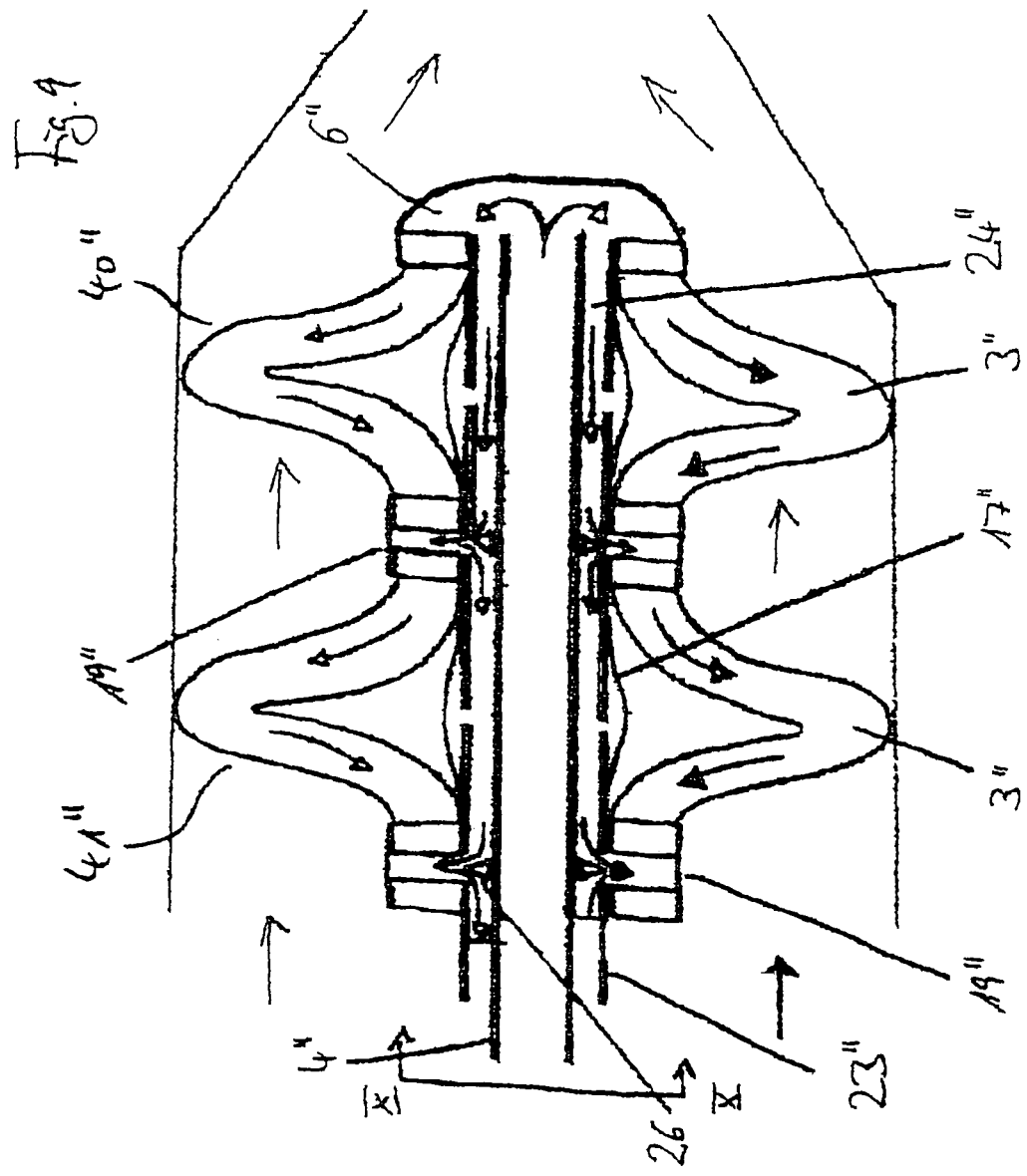
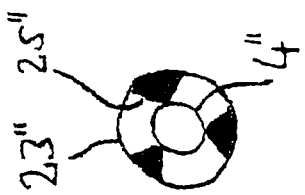

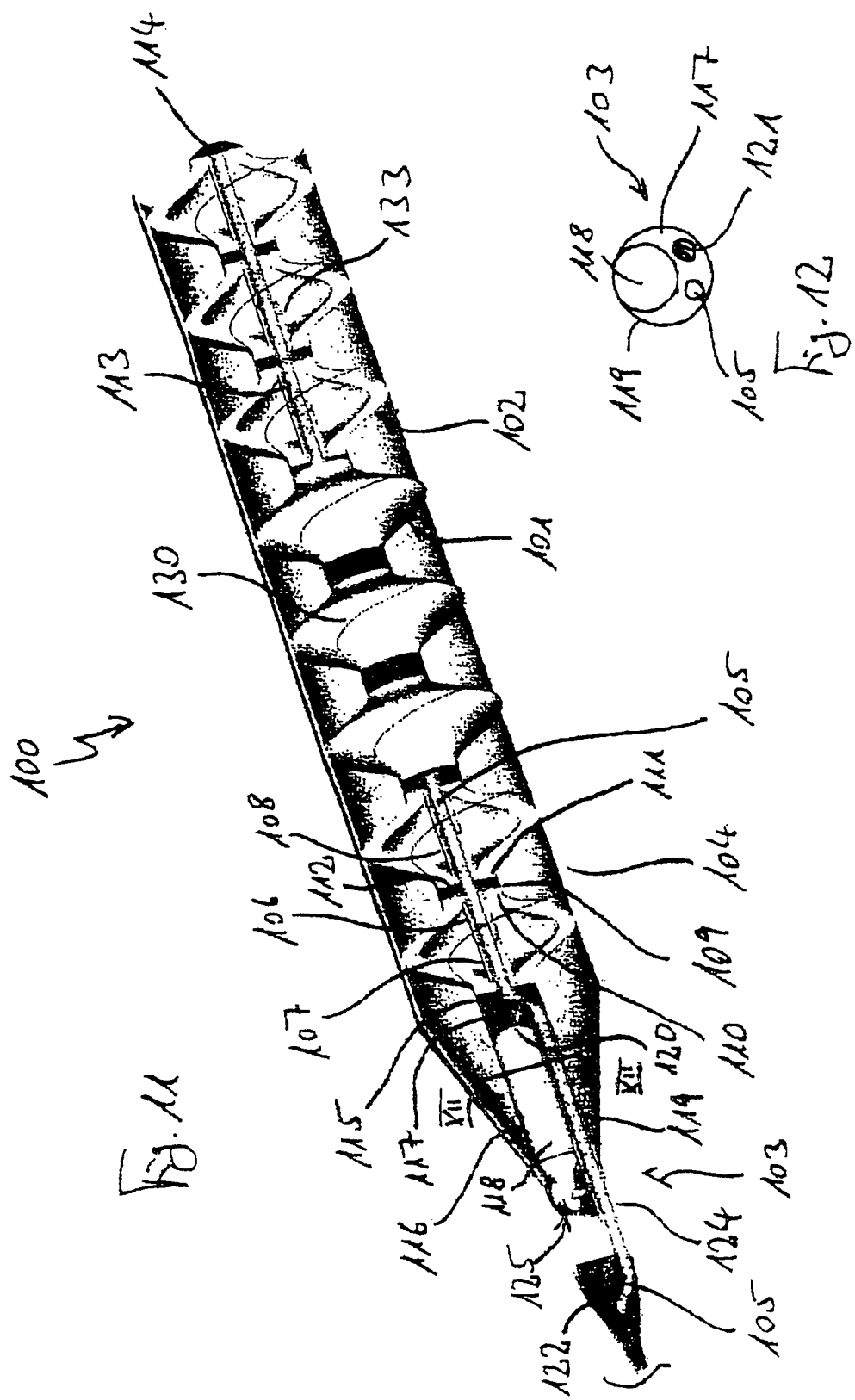

INTRAVENOUS OXYGENATOR WITH IMPERMEABLE SHEATH AND WIRE GRATE

CROSS REFERENCE TO RELATED APPLICATIONS

Applicants claim priority under 35 U.S.C. §119 of German Application No. DE 102 33 290.8 filed on Jul. 22, 2002 and German Application No. DE 102 47 629.2 filed on Oct. 11, 2002. Applicants also claim priority under 35 U.S.C. §365 of PCT/DE2003/002455 filed on Jul. 22, 2003. The international application under PCT article 21(2) was not published in English. Applicants also claim priority under 35 U.S.C. 120 and 35 U.S.C. 121 because this is a Divisional Patent Application of U.S. patent application Ser. No. 10/522,331 filed Jan. 24, 2005, which is a 371 of PCT/DE2003/002455 filed Jul. 22, 2003. U.S. patent application Ser. No. 10/522,331 has issued as U.S. Pat. No. 7,641,853 on Jan. 5, 2010.

The invention relates to an intravenous oxygenator, more specifically to an intravenous oxygenator having an integrated blood pump.

In the field of the clinical therapeutic treatment of patients with impaired lung functions, the regular objective is to assist the lung in its primary function, which is to enrich the blood with oxygen in exchange for carbon dioxide.

In intensive care medicine, acute respiratory failure is one of the most frequent diseases worldwide. It manifests as an insufficient exchange of oxygen and carbon dioxide and is, as a result thereof, seriously life-threatening and involves an enormous amount of staff and expense needed for treatment. Despite intensive research and novel therapies, the acute respiratory failure still exhibits very high mortality rates of from 50 to 70%.

Early respiratory failure constitutes for example another impairment. Early respiratory failure is one of the main causes of high mortality in lung transplant recipients. Approximately one fourth of the patients die in the first year following lung transplantation.

Mechanical ventilation is the standard therapy for both acute and early respiratory failure. Meanwhile, it is however recognized that mechanical ventilation considerably damages the lung tissue since the high pressures and volumes needed for mechanical ventilation may result in excessive lung distension and accordingly in a mechanical destruction of still healthy lung regions. The extracorporeal membrane oxygenation was developed as an alternative thereto. Here, an extracorporeal circuit in which the blood is enriched with oxygen and relieved of carbon dioxide in an artificial oxygenator consisting of fibers is made use of. The blood is drawn from a large vein, moved through the oxygenator by a pump and returned to the large vein.

With this therapy, surgery is unfortunately very invasive and the risk of hemorrhage accordingly high. Moreover, the intensive contact of the blood with artificial surfaces promotes thrombus formation and damages the blood cells.

Intravenous, implantable devices for oxygenating the blood have been investigated as a remedy for approximately 15 years. In such a solution, there is only very little contact between the blood and the artificial surfaces. In this therapy, the oxygenator is introduced through a femoral vein in the leg and is positioned in the inferior vena cava.

The oldest document, U.S. Pat. No. 4,583,969, discloses a membrane oxygenator intended to be positioned in the inferior vena cava. The oxygenator comprises a bundle of 1,200 hollow fibers approximately 50 cm in length. Oxygen is directed through the hollow fibers so that oxygen is caused to pass into the blood and carbon dioxide into the hollow fiber by pure gas diffusion. The bundle of fibers however disadvantageously offers high flow resistance so that the blood may collect at a plurality of sites and may result in thrombus formation there. Moreover, gas exchange is reduced, which is due to the fact that the blood is but insufficiently mixed as a result of the substantially parallel arrangement of the fibers. Herein after, all of the further developments are based on an improved configuration of fibers and flow. More specifically, the breakthrough was considered achieved by increasing the velocity of the blood and by causing it to flow perpendicularly against the fibers. However, perpendicular flow against the fibers and thorough blood mixing result in a high flow resistance.

To compensate this, the document EP 0 507 724 A1 proposes an intravenous oxygenator in which the fibers also lie alongside the vein, but in which a pulsating balloon is arranged in the center of the fibers alongside the longitudinal axis of the oxygenator, said balloon urging the blood through the fibers at right angles to the longitudinal axis. The balloon however occupies quite a lot of space, thus reducing the number of possible fibers to such an extent that approximately but one fifth of the required gas exchange is achieved.

U.S. Pat. No. 5,037,383 proposes an intravenous oxygenator in which the blood flows with high velocity perpendicularly against the fibers except for small border regions thereof. Although this is beneficial to gas exchange, it causes very high pressure losses of up to more than 100 mmHg mercury column.

In an effort to resolve the problem of high pressure drop, U.S. Pat. No. 5,814,011 discloses an oxygenator comprising, in a laterally impermeable sheathing, the gas exchange fibers and a blood pump. The pump creates a local pressure differential within the sheathing so that the blood is allowed to flow through the fibers at high pressure and to thereby reduce energy to such an extent that it may be reintroduced into the vein without damage upon exiting the sheathing. It was not possible to achieve the required amount of gas exchange with this approach either. An urgent need remains for a particularly suited constellation of fibers and/or flow.

It is the object of the invention to provide an oxygenator having improved gas exchange properties.

This object is achieved by an intravenous oxygenator having a bundle of fibers allowing through flow of oxygen and carbon dioxide therealong, said fibers being each connected to a gas supply means through a first connection and to a gas evacuation means through a second connection so that oxygen and carbon dioxide are allowed to flow through the fibers from the first connections to the second connections, said oxygenator being characterized in that the fiber bundle is twisted during operation by relative rotation of the first connections relative to the second connections of the fibers about a longitudinal axis of the oxygenator.

The selective, at least substantially parallel twisting of the fiber bundle has a particularly beneficial effect onto the flow pattern of the blood. On the one side, twisting effects that the fibers are more densely packed. A lot of elongated, very flat slots form between the fibers as a result thereof, said slots acting as flow channels for the blood. The blood flows with very high speed through these flow channels as a result of the flow continuity provided and considerably reduces Stokes' adherence range through increased turbulence. This results in a surprisingly increased gas exchange. Through twisting, the fibers themselves serve as a means for directing the blood flow longitudinally through the narrow flow slots. In radial extension, the fibers may hereby have a shape approximately corresponding to the shape known from U.S. Pat. No. 5,037,383. There, the fibers form loops which take their departure from a central catheter disposed on the longitudinal axis of the oxygenator. The loops extend from the center of the oxygenator outward where they are curved at approximately 180° to return back to the center. At the inflection, the curvature is not allowed to be too sharp as this would cause the fibers to bend and to become closed or at any rate the flow resistance to increase considerably. As a result, the fibers extend, at least over a short portion, approximately parallel to the longitudinal axis of the oxygenator.

In the twisted fiber bundle of the invention, by contrast, there is absolutely no risk that the fibers bend too much at the inflection and become closed as a result thereof. The fibers rather begin to bend already in circumferential direction as they extend outward and at the inflection extend over a quite long distance substantially along the circumference perpendicularly to the longitudinal axis of the oxygenator. This permits to advantageously prevent them from bending too much on the one side. On the other side however, the fibers are still perpendicular to the longitudinal axis at the inflection, meaning that, in operation, they are still arranged in a cross-flow pattern relative to the blood flow. Therefore, the invention permits to spread out the fibers substantially perpendicularly to the longitudinal axis over nearly their entire extension between the connections—except for a few millimeters in direct proximity to the connections if said connections are not perpendicular to the longitudinal axis. Accordingly, the blood is allowed to flow against the fibers over almost the entire length thereof in a cross-flow pattern, which further improves the effect of gas exchange. Advantageously, twisting may be such that the connections are relatively rotated from 90° to 300°, preferably from 150° to 270°, more preferably about 240°, per 35 mm running fiber length. Comprehensive tests have shown that with such a twisting oxygen and carbon dioxide exchange is particularly effective. The observation on which this method relies and which implies that twisting the fiber bundle enhances diffusion only applies up to a twisting threshold value. Above this threshold, diffusion decreases again.

As an alternative or in addition thereto, it is advantageous if at least a multiplicity, preferably at least a plurality, of fibers are inclined, in their extension between the connections, at an angle of from 30° to 75°, preferably of from 42° to 71°, particularly of about 62°, to the longitudinal axis if the longitudinal axis and the fiber orientation are projected onto a projection cylinder that is coaxial with the longitudinal axis.

With a twisted bundle of fibers, the connections of a fiber are rotated about the longitudinal axis of the oxygenator by the angles of rotation indicated herein above. The fibers may be mounted to the connections in a variety of ways, for example so as to be free to rotate or firmly clamped. If the fibers are connected so as to be free to rotate, twisting the bundle of fibers will cause the mounting position to rotate such that the fibers extend substantially directly from one connection to the other, except for the radial orientation, meaning the distance between fiber and longitudinal axis. Developing the surface area of a projection cylinder that is coaxial with the longitudinal axis will result in obtaining the two connection point projections being spaced a different distance from the projected straight line of the longitudinal axis. The direct extension of the fiber from one connection to the other is made manifest by the fact that the fiber projection is at least substantially a straight line.

For clamping the fibers to the connections, a clamping type may be taken into consideration in which the fiber ends are mounted parallel to the longitudinal axis. Twisting a bundle of such fibers will not result in a straight line in the projection of the fiber orientation but substantially in a central symmetric curve with two opposing curvatures. At the first connection, the fiber is oriented to be parallel to the longitudinal axis both in space and in projection as a result of clamping. It is immediately curved, said curvature having the same direction as the rotation of the opposite connection. In projection, this manifests as a curvature toward the projection of the longitudinal axis and away therefrom, depending on whether the projection of the opposite connection is nearer to the projection of the longitudinal axis than the projection of the outgoing connection or whether it is farther away. The fiber orientation has a point of inflexion located approximately at the center from where it extends toward the opposite connection in a curvature oriented in the opposite direction until, upon reaching said very opposite connection, it is again parallel to the longitudinal axis.

Evaluation of complex tests showed that the proposed angles between the fiber projection and the longitudinal axis projection yield very good results with regard to diffusion of oxygen and carbon dioxide in the fiber, more specifically if, over the major part of their length, the fibers are in the angular range mentioned. They differ to a surprising extent from the hereto before most effective fiber configuration according to which the fibers project simply radially from the longitudinal axis of the oxygenator so that the flow reaches them at right angles. It should be noted that perpendicular flow against the fibers also be readily achieved with the presently proposed configuration by inclining the fibers in their radial orientation, which does not reflect in the cylinder projection, at a large angle to the longitudinal axis. In their radial orientation, the fibers may for example be curved outward, clearly away from the oxygenator, adopt an angle of about 90° and extend outward maintaining this angle until reaching a certain distance not too short of the half of the fiber length. At the half of the fiber length, there may be a range of inflection where the curvature is generally about 180°, said inflection causing the fiber to extend back inward at right angles, meaning toward the longitudinal axis of the oxygenator. In the range of inflection, the fiber may, as explained herein above and more specifically for example at the circumference of the bundle of fibers, extend at right angles to the longitudinal axis of the oxygenator, so that the fiber segment may also be available for cross-flow in the range of inflection. At a short distance from the opposite connection, the fiber would again have a curvature of about 90° in order to enter the connection mounting parallel to the longitudinal axis. As a result of such an arrangement the flow against the fibers is advantageously mainly perpendicular, with the bundle of fibers being simultaneously twisted.

Independent of the exact orientation of the fibers it is proposed that the bundle of fibers rests against an impermeable sheathing. An impermeable sheathing about the bundle of fibers strongly channels the blood flow and is thus capable of forcing the blood through the fibers. If a gap forms between the bundle of fibers and the sheathing, the blood flow spreads according to the flow resistances over the entire flooded space, meaning, there is only little blood that flows with low velocity through the fibers while great amounts of blood flow with high velocity past the fibers outside thereof and without possible gas exchange with the fibers. This is avoided if the sheathing externally surrounds the bundle of fibers in immediate proximity thereto. For this purpose, the sheathing may more specifically be elastic so as to contract automatically until frictional connection with the bundle of fibers is achieved or so as to follow the extension of the oxygenator.

In order to be capable of absorbing a large amount of blood, it is advantageous to provide the twisted bundle of fibers with the largest possible dimensions. It is however dangerous to have the entire vena cava filled out with the bundle of fibers since clogging of the fiber bundle or failure of the blood pump would largely hinder blood circulation. In an advantageous embodiment of the present invention the twisted bundle of fibers therefore has a diameter of 15 to 30 mm, preferably a diameter of 15 to 25 mm. According to literature, the human vena cava has a diameter of about 30 mm. The applicant performed more accurate measurements which yielded considerably smaller diameters, though. Accordingly, with the known oxygenators, the vena cava would be completely filled out. The present invention may differ therefrom. On the one side, with the fiber configuration proposed, gas exchange is so efficient that higher gas exchange values are obtained even if the cross-section is reduced as compared to prior art oxygenators. On the other side however, the fact that blood may flow to a certain extent around the oxygenator also advantageously allows blood entering the vena cava on the side of the oxygenator to flow in a direction counter to the actual flow direction along the surface area of the oxygenator on the outside thereof. Accordingly, depending on the length and the exact position of the oxygenator, blood may for example be caused to flow from the liver into the vena cava downstream of the oxygenator entrance with respect to the actual flow direction. If the blood is allowed to sufficiently flow around the oxygenator, it may at least partially flow along with the flow entering the oxygenator upstream thereof. As a result, an increased blood flow may flow through the oxygenator.

A radially deformable housing may be provided to accurately define the oxygenator. The impermeable sheathing may also be applied thereto. In order to reliably fix the maximum diameter, it is proposed that the housing be provided with a maximum diameter of 30 mm at the most, more specifically of 15 to 25 mm at the most. For this purpose, the housing may be constructed such that its structure has a perimeter tie rod the length of which matches the largest diameter. As far as possible, the tie rod should be non-elastic, whereas the housing and/or the sheathing may be very elastic, more specifically across the longitudinal axis. Expansion of the housing causes the tie rod to tension until said tie rod does not allow further expansion of the perimeter. If the volume of the housing continues to increase, a non-elastic perimeter restriction causes the housing to adopt a circular shape in cross-section in the region of the tie rod since, with the circular shape, the ratio surface to perimeter is at its maximum. A housing having an integrated tie rod may be represented particularly easily by a wire grate.

Alternatively, the impermeable sheathing may be configured such that it only permits expansion up to a predetermined limit without any external perimeter restriction means. If a pump generates in the oxygenator a pressure that is higher than the blood pressure, such a sheathing is already sufficient to act as a housing for the oxygenator. The excess pressure causes the sheathing to expand into the blood until the expansion force originating from the pressure differential is equalized by the addition of a sheathing-immanent reduction force—for example an elastic tangential tensile force—and the sheathing comes to a standstill in a stable equilibrium of forces. Polyurethane or silicone for example may be well suited for the material of such a sheathing.

As an alternative or in addition to the afore-mentioned, it is proposed that the connections of the twisted bundle of fibers be secured against untwisting themselves. For operation of the oxygenator of the invention, the twisted constellation should be kept as constant as possible. Forces that induce untwisting may however act onto the bundle of fibers. The forces may have an external origin; they may for example be induced by friction against the wall of the vein or by the impulse force of the blood flow when the same is redirected from a flow path along the vein at the bundle of fibers to a rotating secondary flow. The forces may however also be generated within the oxygenator, for example by the restoring force of the fibers when these are clamped to the connections and have, in their condition at rest, a shape different from the one in the twisted condition. By securing from untwisting it is made certain that the bundle of fibers will not depart from the configuration of the invention without conscious human intervention.

It is thereby advantageous if the bundle of fibers is only secured against untwisting up to a limit force. When the oxygenator is in its operating position, opposing moments may be applied to the connections by a suited communication with the outside, for example by rotating in opposite directions two interlocked catheters with the outer catheter being connected to the one connection and the inner catheter to the other connection so that the moments match. Accordingly, even in operation, moments may be applied to the oxygenator, said moments being limited substantially only by the twisting resistance of the catheters. Therefore, securement against rotation may be implemented in such a manner that, if a limit force is exceeded, namely preferably a limit force that is so high that in all probability it will only occur when the connections are consciously rotated, it yields to the rotation. The terms "limit force" and "limit moment" are understood to be equivalent in meaning because the limit moment is defined through the limit force as a product with a force lever of the limit force.

As an alternative and in addition thereto, it is advantageous if means for limiting further rotation of the connections of the twisted bundle of fibers relative to each other are provided. Like the forces acting to untwist the twisted bundle of fibers, internal and external forces acting to further rotate the connections may also occur. The very fibers limit possible rotation of the connections for, if the fibers are completely stretched, i.e., around the oxygenator, further rotation can only occur upon rupture of the fibers; it is however proposed to provide means for stopping further rotation already before the fibers are stretched or for hindering rotation up to a limit force like explained herein above in connection with untwisting. A particular advantage is achieved if, in the optimum constellation of the invention, the bundle of fibers is secured in both directions up to a limit force.

In terms of construction, particularly reliable securement of the type described may be achieved by providing a frictional connection between a first fiber holder and a second fiber holder, said fiber holders being connected to the connections. Accordingly, the function of securing the connections is transformed into the function of securing the fiber holders against rotation, with more space being available therefore than at the connections if the fiber holders are suitably configured.

According to an advantageous embodiment, the fiber holders are disposed in the inner volume of the bundle or bundles of fibers. They may more specifically be sliding bodies shaped like a cylinder jacket that surround a central catheter on which they are slidable along the longitudinal axis of the oxygenator, which may be appropriately formed by the central catheter. If a sliding body in the shape of a cylinder jacket is disposed directly inside on a fiber connection, the orientation of the fibers is not affected by the fiber holder. In this case, the holding device only serves to radially fix the connection. The fiber ends on the fiber outer surface may be sweat soldered and their front surfaces may be connected to the gas supply means or to the gas evacuation means with gas supply means and gas evacuation means providing a hollow annular chamber at the respective one of the connections. On the inner side of the ring, said chamber may be simply mechanically connected to the fiber holder, such as by gluing. A fiber holder in the shape of a cylinder jacket is moreover particularly free to rotate about the central longitudinal axis, more specifically relative to an adjacent fiber holder of the same bundle of fibers, meaning of that fiber holder that retains the opposite end of the fibers or their connection.

It is understood that a chamber of the type proposed needs not be an independent component. The chamber may rather also be embodied by a space between two fiber connections for example. In this case, it is proposed to delimit and seal this space from the outside with a sheathing that is more specifically shaped like a cylinder jacket. The fibers of two adjacent bundles of fibers may be introduced in opposite directions into the sheathing to such an extent that a cavity remains between the front ends of the fibers. Said cavity may be appropriately connected to the gas supply means and/or to the gas evacuation means.

An oxygenator with fiber connections that are individually connected to fiber holders which are mounted so as to be rotatable relative to each other about the longitudinal axis of the oxygenator is advantageous and inventive by itself already.

In a preferred embodiment, the oxygenator proposed comprises a substantially or even pronounced elastic connection between two neighboring fiber holders of the same bundle of fibers in the longitudinal direction of the oxygenator. Advantageously, during deformation of the oxygenator, restoring energy is thus automatically stored in the elastic bond. A bond that allows for relative rotation of the fiber holders by applying a force or a moment while the counterforce or the opposing moment increases is more specifically to be envisaged.

The force or the moment applied may be generated by rotating two catheters in the manner described herein above so that the elastically bound fiber holders are brought from a condition at rest in which the bundle of fibers is not twisted into the twisted condition of utilization. In this case, the surgeon would benefit from the fact that the oxygenator will not tend to rotate during insertion thereof into the vena cava nor during subsequent removal. Twisting would only be performed and fixated at the site of utilization by the surgeon. For removal, the surgeon would only need to remove the fixation for the oxygenator to return to its untwisted shape. Alternatively, the bundle of fibers can be twisted in its condition at rest. In this case, the surgeon would have to prevent rotation during insertion and during removal, for example by clamping the two catheters together, but in use the fiber bundle would always be twisted and held without an external force. The condition at rest can be characterized in that there is equilibrium of moments between the fibers and the force-transmitting bonds between the connections. In case the bundle of fibers is twisted in its condition at rest, it is proposed that, with a relative rotation of from 90° to 300°, preferably of from 150° to 270°, more preferably of about 240°, per 35 mm fiber length, the condition at rest is located between the two connections. These are the values that have been discussed in detail already and at which gas exchange is surprisingly important.

An elastic bond between two fiber holders of the same fiber bundle, or rather between two neighboring connections in general—if a plurality of fiber bundles is provided one behind the other along the oxygenator—may particularly suitably comprise a membrane and/or a linear spring. A membrane permits in a particularly simple manner to transmit moments between the fiber holders of the same fiber bundle. If the membrane, in the form of a closed cylinder jacket, spans the distance between two neighboring fiber holders that are also shaped like a cylinder jacket, one furthermore obtains a structure that seals the inner volume from the outside where the blood impinges upon the fibers. As a result, the structure consisting of fiber holders and connection membranes can be used for supplying or evacuating gas so that there is no longer need for a catheter in the longitudinal orientation of the oxygenator, which allows a more compact and less expensive construction.

It should be noted that an oxygenator with an elastic membrane bond between the fiber holders—more specifically if, thanks to the bond, a sealed inner volume is formed—is advantageous and inventive independent of the remaining advantageous features of the present invention.

A linear spring may more specifically be provided with a condition at rest that is different from that of a membrane in order to counteract the forces of the membrane and to thus per balance reduce the elastic forces within the oxygenator. As a matter of course, a linear spring can also be used to advantage independently of a membrane. More specifically, a linear spring may even be disposed parallel to the longitudinal axis between two fiber holders and urge apart the fiber holders so that a tensile force is applied onto the central catheter. This prevents in the best possible way the central catheter from bending. A linear spring or a curved spring may also serve to rotate the fiber holders relative to each other. If a membrane is also present, it may always be kept slightly tensioned as a result thereof. If slack develops in the membrane, folds may form in which blood may collect, which increases the risk of blood clot formation.

If the oxygenator has a plurality of fiber bundles arranged in series, it is proposed that they be all twisted in the same direction. The blood exerts a force onto the fibers spread into a layer, thus deforming the same. Depending on the turbulence and on the homogeneity of the flow, regions may form in which the fibers are for example too close so that the blood will find it difficult to flow through them. In view of this problem, it may be appropriate that the fibers have but the smallest possible length between two fixed fiber points, for example the connections. A constellation in which a plurality of fiber bundles are connected in series and twisted in the same direction has the advantage that the flow generated along the fibers over a long distance of the blood flow is particularly good without the various fibers becoming too unstable or so long that the gaseous mixture of oxygen and carbon dioxide flowing therein becomes too rich in carbon dioxide. In the case of a plurality of fiber bundles accordingly having a plurality of connection pairs, oxygen supply may occur at each first connection. A stable structure consisting of a very large quantity of fibers may be provided, which advantageously implies a large overall fiber surface.

Arrangement of a plurality of fiber bundles on separate fiber holders is particularly preferred for, by rotating one bundle of fibers, a torque is also transmitted onto the neighboring bundles of fibers. Without any further intervention, uniform torque distribution is thus obtained so that all of the fiber bundles are twisted in the same way, being thus joined together.

Even irrespective of the afore mentioned, an oxygenator having fiber holders that are rotatable relative to each other is advantageous and inventive, said oxygenator being characterized by a first driver provided on the first fiber holder and a second driver provided on the second fiber holder, said fiber holders being directed toward each other and allowing rotation of the first fiber holder relative to the second fiber holder at least in one direction of rotation up to a rotation limit only without the second fiber holder being carried along when the two fiber holders are disposed in a coaxially aligned relationship and are pressed into contact with each other. If two such matching drivers are provided, it is particularly easy for the surgeon to twist the bundle of fibers in accordance with the invention—more specifically even a bundle of fibers that is untwisted at rest—without seeing the oxygenator. When the bundle of fibers is actively rotated, the required moment is not allowed to increase substantially, or at least only approximately linearly. As soon as the rotation limit is achieved, the drivers at the sides facing each other cooperate to provide the surgeon with haptic feedback that the desired twist is achieved true to size. Preferably, two fiber holders of neighboring bundles of fibers may be connected with zero clearance.

With regard to the identified condition of rotation for optimum gas exchange, the rotation limit should be at a relative rotation of from 90° to 300°, preferably of from 150° to 270°, more preferably at about 240°, per 35 mm fiber length.

An abutment device is also proposed to be provided on the fiber holders, also in the longitudinal direction, for limiting relative displacement of the connections. Such an abutment device may for example be directly embodied by the fiber holders, given the latter protrude far enough from under the connections to prevent two neighboring fiber connections from abutting against each other or the fibers from bending when the fibers are being spread by causing the connections to move together along the longitudinal axis.

In order to allow the bundles of fibers to be twisted in a simple manner and to an extent that may be precisely predetermined when the connections are caused to move together, a spiral guidance means may be provided for the connections and/or the fiber holders, irrespective of the afore mentioned. The spiral guidance means may more specifically be disposed at the central catheter and cooperate for example with the fiber holders in the form of a thread having a large pitch.

In a preferred embodiment, the oxygenator comprises a gear that is connected to a bundle of fibers. Such a gear may for example indicate the rotation angle of a connection, more specifically of the first bundle of fibers if a plurality of fiber bundles is connected in series. The surgeon may thus objectively perceive the angle at which he already caused the first connection to rotate.

It is more specifically suggested that, on a rotation device for twisting a plurality of fiber bundles connected in series, a gear be provided between the rotation device and a bundle of fibers in such a manner that the gear transmits a rotation of the rotation device—for example a rotation wheel—onto the bundles of fibers at a ratio corresponding to the number of fiber bundles or to the ratio of the overall length of the bundles of fibers to a scale length. In the oxygenator, ten to fifteen bundles of fibers having each the same fiber length of 35 mm may be present for example. Given the ratio of transmission of the gear corresponds to the number of fiber bundles and the neighboring bundles of fibers are suitably connected together, all of the bundles of fibers would be twisted by the angle of rotation that was rotated but once on the rotation device. A gear with a ratio of transmission of 10:1 for example transmits a rotation of the rotation device by 240° onto the connected connection so that the latter is rotated 240°. If the connections of neighboring bundles of fibers are suitably connected— more specifically as explained in connection with the fiber holders—each bundle of fibers is twisted about 240° if ten bundles of fibers are provided. As a result thereof, the surgeon is capable of particularly well adjusting the twist in ªvery controlled manner and with but little movement of his own without seeing the oxygenator during twisting.

It should be noted that all of the features that have been described as ling advantageous are advantageous and inventive in any alternative or cumullion and this also independent of a twist of the bundle of fibers.

Figure 2:
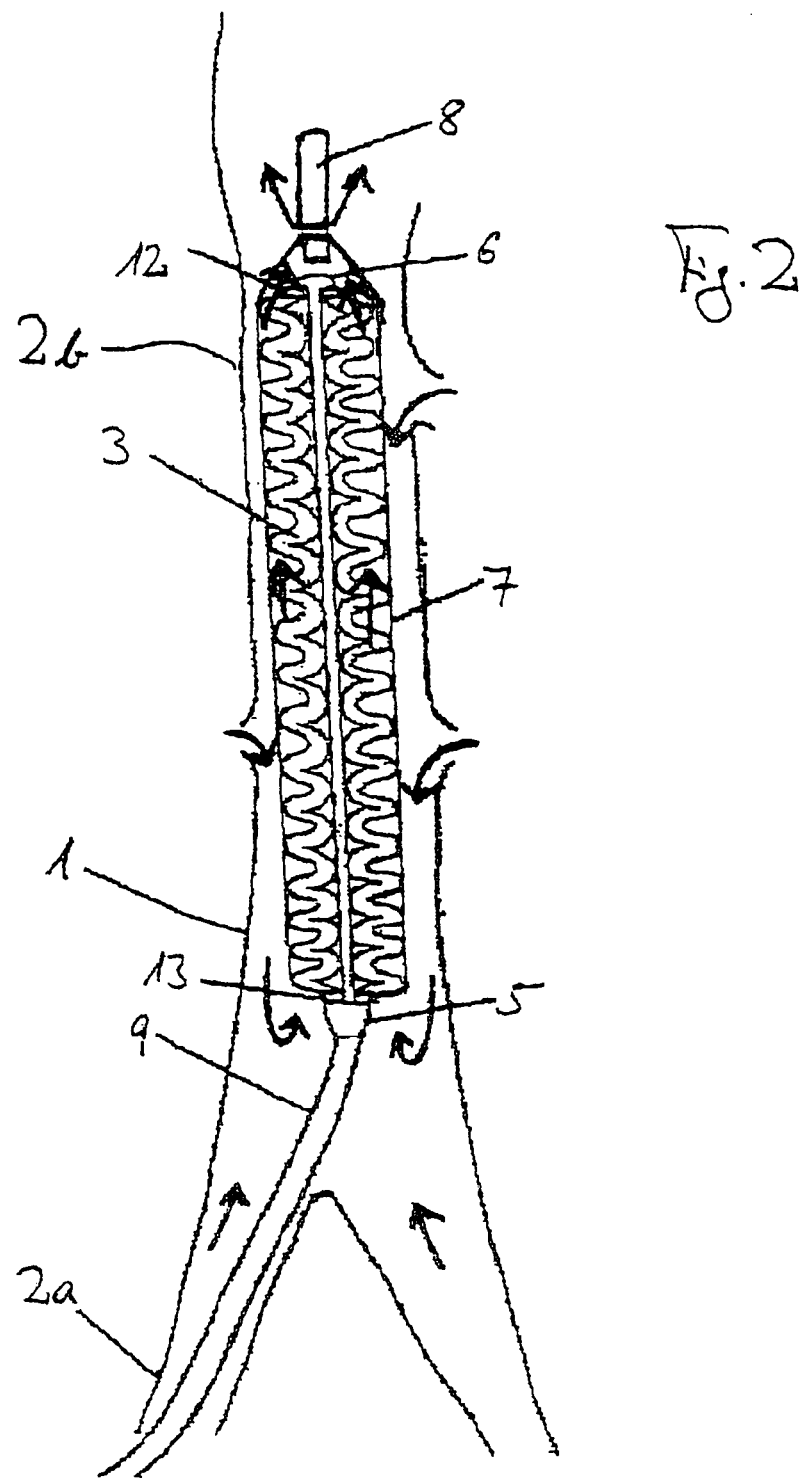
Figure 3:
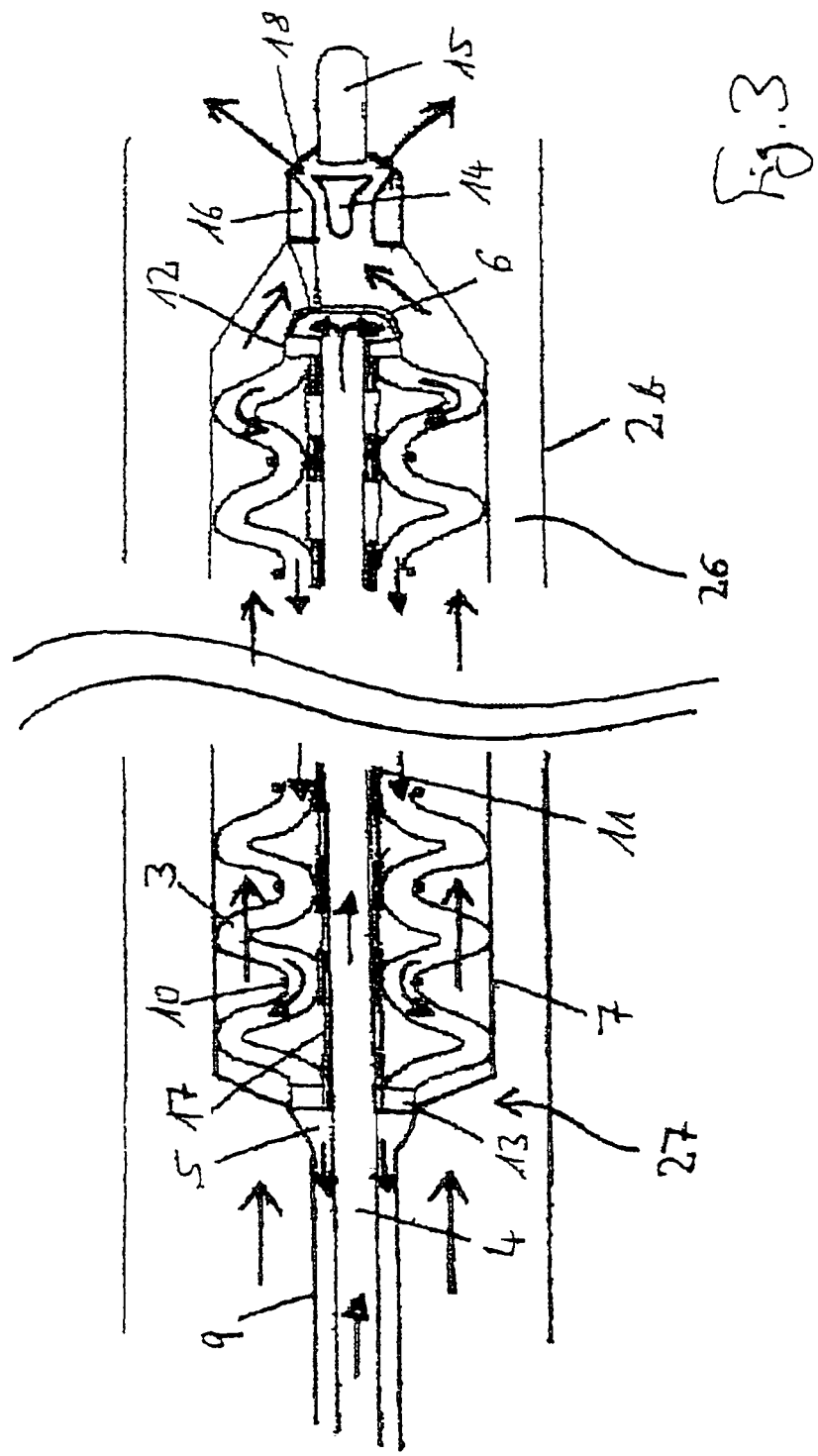
Figure 4:
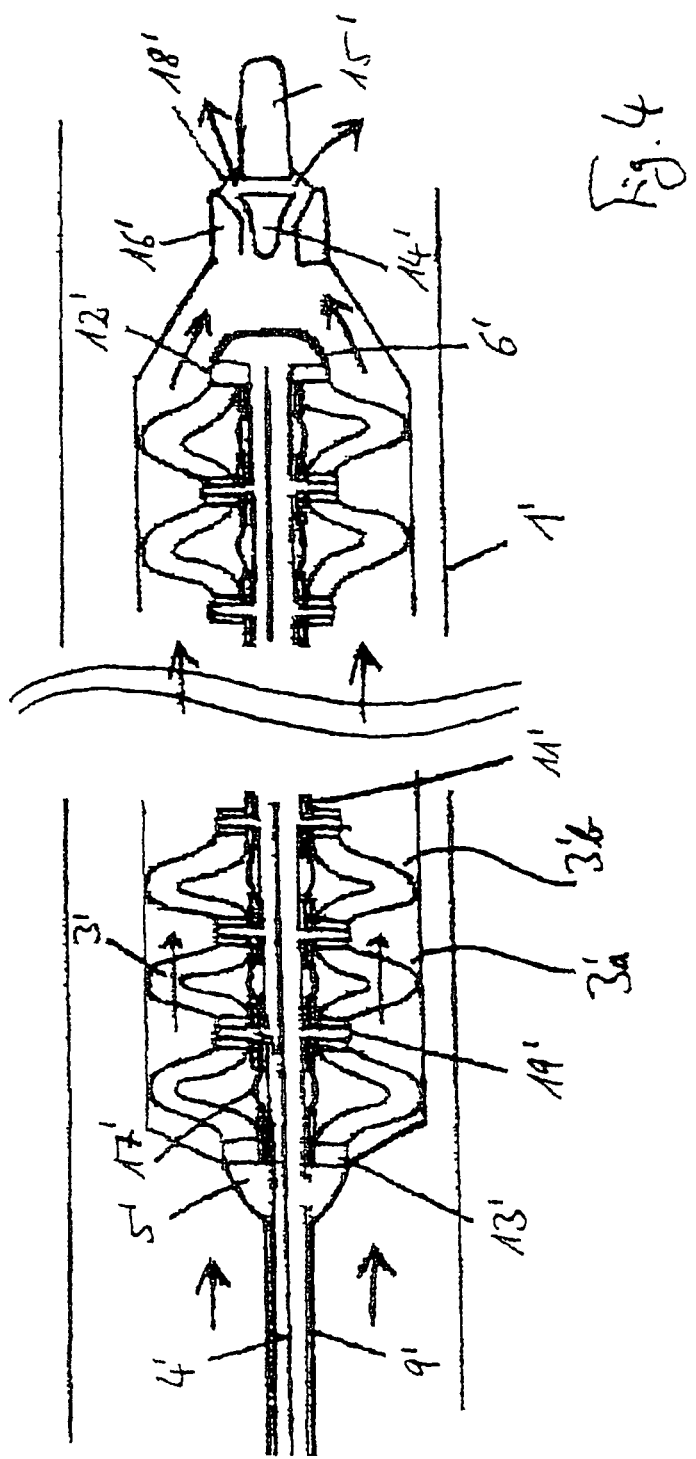
Figure 5:
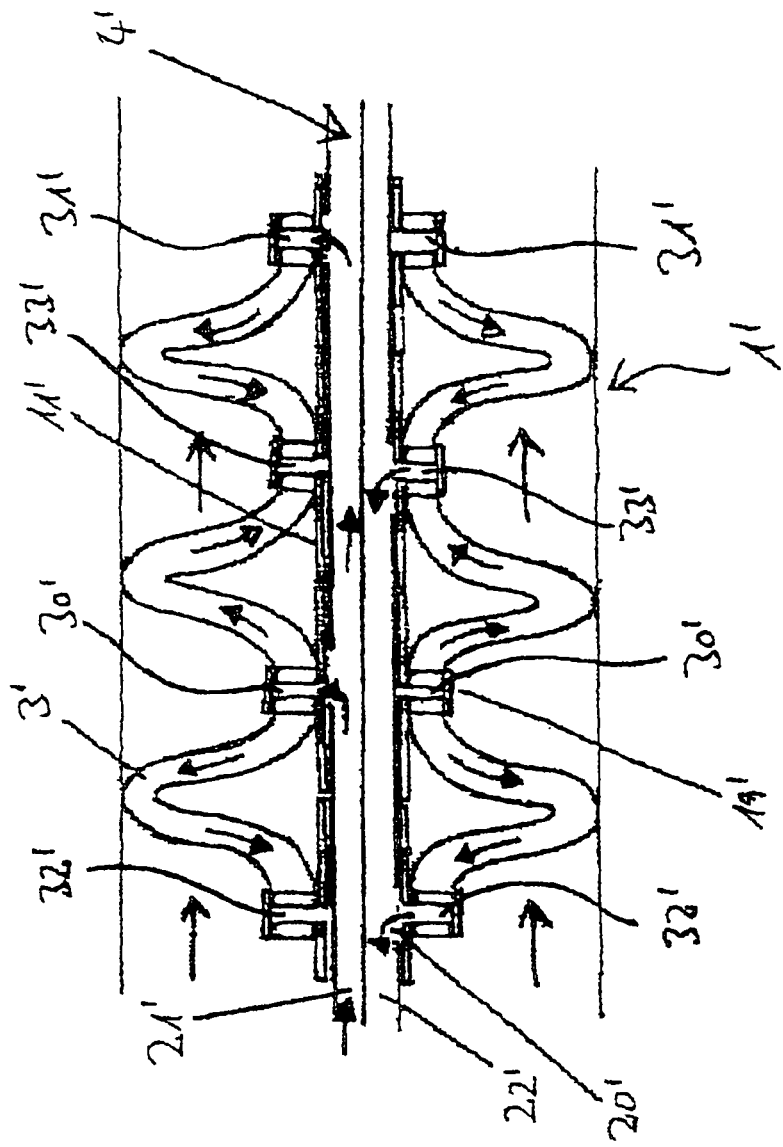
Figure 6:
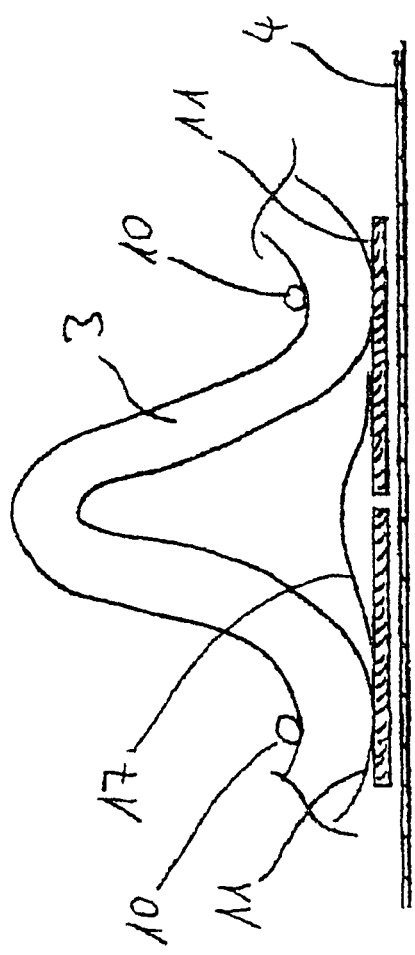
Figure 7:
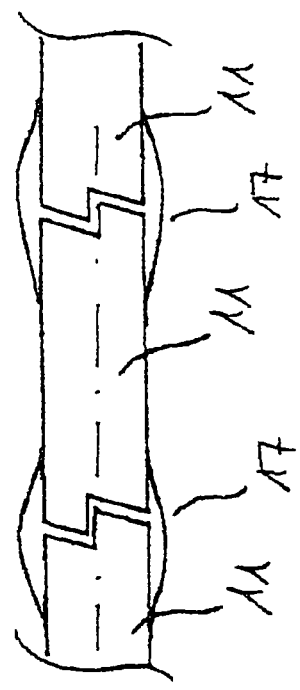

The invention will be understood better upon reading the following description of exemplary embodiments, given with reference to the drawing. Like reference numerals may thereby designate like or similar elements. In the drawing:

FIG. 1 schematically shows a folded oxygenator that is being introduced through a femoral vein, FIG. 2 schematically shows the oxygenator of FIG. 1 unfolded in a vena cava, FIG. 3 schematically shows a sectional view of the oxygenator of FIG. 2 illustrating the gas flow, FIG. 4 schematically shows a sectional view of an alternative oxygenator having fibers divided into a plurality of units connected in series, FIG. 5 shows a detail of the schematic view of FIG. 4 illustrating the gas flow, FIG. 6 shows a detailed sectional view of two neighboring and connected cradles for holding the fibers, FIG. 7 is a top view of an arrangement of a plurality of cradles that are rotated relative to each other, FIG. 8 schematically shows a sectional view of another oxygenator with modified gas guidance, FIG. 9 is a detail view of the other oxygenator of FIG. 8 with the gas flow being indicated, FIG. 10 is a top view of the cradles of the FIGS. 8 and 9 taken along section line X-X in FIG. 9, FIG. 11 is a longitudinal sectional view of an oxygenator with a pump unit disposed upstream thereof and FIG. 12 is a cross-section on the line XII-XII of FIG. 11.

The oxygenator 1 in the FIGS. 1 through 3 is introduced through the femoral vein 2a and is positioned in the vena cava 2b. Because of the limited insertion space, fibers 3 intended for gas exchange are folded during insertion and lie alongside a central catheter 4. In this configuration, the diameter of the oxygenator is very small and matches the anatomic size of the femoral vein 2a.

The catheter 4 is a commercially available implementation and has the mechanical properties required for medical applications. The bundle of fibers 3 is respectively connected at its ends to a supply chamber 6 and to an evacuation chamber 5 that hold the bundle of fibers 3 together and simultaneously act as connections 12, 13 for receiving the fibers 3 in such a manner that gas is allowed to flow from the supply chamber 6 through the first connection 12 through the fibers 3 and the second connection 13 to the evacuation chamber 5.

A housing 7 with a round cross-section surrounds the bundle of fibers 3. The cylindrical housing 7 has a carrier structure in the form of a deformable wire grate capable of expanding to a maximum diameter which is slightly smaller than the diameter of the vena cava 2b. The wire grate is connected to an impermeable elastic sheathing that also deforms along with the grate.

At an end of the bundle of fibers 3, a microaxial pump 8 is connected to the housing 7 and the supply chamber 6. A flexible tube 9 is connected to the other end of the bundle of fibers 3. The flexible tube 9 surrounds a (non-visible) portion of the central catheter 4 that extends outward as a continuation thereof. The flexible tube 9 concurrently non-sealingly engages the housing 7.

The fibers 3 are sweat soldered at the connections 12, 13 but have free front surfaces for connection with the chambers 5, 6. The catheter 4 extends centrally through the bundle of fibers 3 and is connected to the supply chamber 6 on the side of the pump. As described, the supply chamber is connected to the bundle of fibers 3 through the first connection 12. At the opposing connection 13, the fibers 3 are connected to the evacuation chamber 5 which in turn is connected to the free space that remains beside the extended portion of the catheter in the flexible tube 9. A gas flow path is thus formed which extends from the catheter 4 via the fibers 3 back to the flexible tube 9.

The flexible tube 9 and the catheter 4 extend beyond the insertion site through the skin, out of the patient's body.

The microaxial pump 8 is connected in series at the end of the oxygenator 1 to the housing 7 and the supply chamber 6. The pump 8 substantially consists of a rotor 14, a motor 15 and a pump housing 16. The blood inlet of the pump 8 is located in the volume within the sheathing 7. The blood outlet is located outside of the sheathing 7. The pumping direction of pump 8 is directed from connection 13 to connection 12, meaning in the physiological flow direction (indicated by simple arrows).

In the unfolded configuration of FIG. 2, the oxygenator is located in the inferior vena cava 2b. The bundle of fibers 3 is spread out in a radial direction and twisted at a plurality of sites. Through spreading the bundle of fibers 3 shortens in length and the surrounding sheathing 7 is expanded to its maximum diameter. In the example shown, the bundle of fibers may be rotated more specifically 240° per 35 mm fiber unit length with the fibers having shortened in length from an initial length of about 30 to 35 mm to about 14 mm. The bundle of fibers may thereby more specifically have 200 to 250 fibers with an overall surface of for example about 0.01 $m^2$. These constellations yielded very efficient gas exchange in tests.

The bundle of fibers 3 of the unfolded oxygenator 1 in FIG. 3 is fastened at regular intervals to the central catheter 4 with thin rings 10. In the region of the rings 10, between the fibers 3 and the catheter 4, there are located guide cradles 11 which hold the fibers 3. By sliding the flexible tube 9 over the catheter 4, the fiber bundle is compressed in the longitudinal direction and is thus spread out. The fibers 3 are thus forced to spread in the spaces between two adjacent rings 10. A plurality of wave-shaped fiber units form as a result thereof.

Thanks to the cradles 11, the fibers can readily slide on the central catheter during displacement of the flexible tube 9 and the associated spreading of the bundle of fibers 3. The cradles 11 thereby have front profiles that are capable of cooperating with the respective profiles of the neighboring cradles 11 (see FIG. 6 in particular).

During compression of the Oxygenator 1, the bundle of fibers 3 can be spread out until the cradles 11 make contact with their respective neighboring cradle 11. As a result, at the end of compression, all of the fiber units have the same length between two rings 10—the bundle of fibers 3 is spread out as homogeneously as possible. The bundle of fibers 3 is twisted by rotating the flexible tube 9. The profile of the cradles 11 is configured such that two neighboring cradles 11 can only be rotated relative to one another up to a maximum relative angle at which two drivers provided at the two cradles 11 prevent further relative rotation. Once maximum rotation is achieved, the two drivers are in frictional contact. Presently, said contact is ensured by an interlocking contact of the two neighboring cradles 11. As a result, each fiber unit between two rings 10 has the same twist.

The space between two cradles 11 is sealed by impermeable membranes 17. On the outside, the fibers 3 are moreover surrounded by housing 7, which is provided with the impermeable sheathing. On one side, housing 7 is sealingly connected to the pump 8 and on the other side non-sealingly to the evacuation chamber 5. By stretching the housing 7 at its ends, it becomes longer and slimmer. The sheathing thereby moves along with the movement of the housing 7. During insertion of the oxygenator 1, the housing 7 is stretched by pulling the flexible tube 9 and, as a result thereof, the evacuation chamber 5 over the catheter 4 away from the pump 8. As a matter of course, a bond on the side of the chamber 5 can alternatively be excluded and the housing or the sheathing simply folded for insertion of the oxygenator.

By displacing the flexible tube 9 in the opposite direction, meaning toward the pump 8, once it has reached its target position in the vena cava 2b, the oxygenator 1 is compressed lengthwise so that the housing 7 and the sheathing expand to their maximum diameter. Once compressed and twisted, the fibers 3 fill out the entire space between catheter 4 and housing 7.

In the exemplary embodiment of the oxygenator 1, the fibers run along the entire length of the bundle of fibers 3 as gas through lines. When the oxygenator 1 is operating, oxygen is supplied through the catheter 4. Oxygen flows through catheter 4 into the supply chamber 6 (gas flow is indicated by closed arrows). From there, oxygen flows via the first connection 12 into the fibers 3 at the surface of which diffusive gas exchange takes place in the blood. Oxygen thereby passes into the blood in exchange for carbon dioxide. At the second connection 13, the fibers contain a gaseous mixture of oxygen and carbon dioxide. The gaseous mixture flows through the evacuation chamber 5 into the flexible tube 9 through which it is led out of the patient's body.

The blood flows in the oxygenator 1 in the region of connection 13, flows against the twisted bundle of fibers 3 within housing 7 and reaches pump 8. There, the blood is urged by the rotor 14 to flow in the flow direction of the vein 2a, 2b and leaves the oxygenator 1 through outlet 18.

As a result of the flow redirection processes experienced while flowing around the fibers 3, the blood looses flow energy. Therefore, the blood pressure directly at the pump is lower than at the oxygenator entrance port on the side of the second connection 13, where the pressure is physiological. The pressure drop is again balanced by the pump 8 so that the pressure at the outlet 18 is again physiological. Outside of housing 7, the blood does not experience considerable pressure loss thanks to a sufficiently large space 26 available for flowing around the fibers, to a front side profile 27 that is formed so as to allow for convenient flow and to the reduced roughness of the flow on the outer side of the housing 7. Accordingly, the pressure inside the housing 7 is lower than that in the surrounding space 26 in the vena cava 2b. As a result, a physiological pressure may be kept up in the vena cava 2b which prevents the organs from being loaded with excess pressure and which allows physiological flow of the blood returning to the heart.

In the alternative embodiment of an oxygenator 1' as shown in the FIGS. 4 and 5, the bundle of fibers 3' is separated into a plurality of units (indicated at 3'a and 3'b by way of example). Between the two following fiber units 3'a, 3'b, there are located toroidal chambers (labeled at 19' by way of example) to which the two fiber units 3'a, 3'b are connected. The oxygenator 1' is unfolded in the same way as oxygenator 1 since the mechanical skeleton structure of the two oxygenators 1 and 1' is the same. Twisting of the bundle of fibers 3'a, 3'b is again performed by rotating the flexible tube 9'. The catheter 4' is a two-lumen catheter and comprises a plurality of openings (labeled at 20' by way of example) on the two lumens 21', 22'. The toroidal chambers 19' are displaced by longitudinally displacing the flexible tube 9'. After displacement has been completed, this is the case when the cradles 11' are contacted, the toroidal chambers 19' are located on the same height as the respectively associated openings 20'. The openings 20' are alternately provided on the two lumens 21', 22' so that every second toroidal chamber 19' coincides with the opening of a respective one of the lumens 21 and 22. In the exemplary embodiment shown in the detail view of FIG. 5, the oxygen supply lumen 21' is connected to two toroidal chambers 30', 31' whereas the gas evacuation lumen 22' is connected to two toroidal chambers 32', 33' via a slot- or point-shaped opening cover.

When the oxygenator 1' is operating, oxygen is supplied through the oxygen supply lumen 21' of the catheter 4'. Oxygen thus enters the toroidal chambers 30' and 31' and from there the fibers 3' where gas exchange takes place in the blood. As a gaseous mixture of excess oxygen and of carbon dioxide removed from the blood flows out of the fibers 3', it enters the toroidal chambers 32' and 33' and from there flows into the gas evacuation lumen 22' through which it flows out of the body.

The seal between two adjacent toroidal chambers can be achieved in a variety of ways, such as by sealing rings. Blood pressure itself may be used for sealing if an elastic membrane surrounds the catheter and is pressed against said catheter by the increased blood pressure, thus sealing the gaseous side, meaning the inner volume.

The other oxygenator 1" depicted in the FIGS. 8, 9 and 10 also comprises a plurality of fiber units that are disposed in series. The catheter 4" is a one-lumen catheter and is connected to the gas supply chamber 6". The discrete bundles of fiber are connected to cradles 23" that are capable of sliding along the catheter 4" and of rotating. An annular channel 24" is located between the cradles 23" and the catheter. The cradles 23" are readily and securely centered on the catheter 4" by means of projections 25".

When the oxygenator 1" is operating, oxygen exiting the gas supply chamber 6" flows in parts into the fibers of the first bundle of fibers 3", but in parts also into the annular channel 24". Neighboring cradles 23" are connected by an elastically deformable membrane 17" so that the channel 24" is sealed. Both oxygen from the channel 24" and the mixture of oxygen and carbon dioxide from the first bundle of fibers 40" enter the ring chamber 19" that connects the first bundle of fibers 40" to the second bundle of fibers 41". The two gas flows blend together, the blending being enforced by flow baffles 26" and by the resulting turbulence and eddies. The flow baffles 26" are provided with a profile that permits the gas from the channel 24" to enter, if possible, the entire depth of the toroidal chamber 19". Through blending, the carbon dioxide concentration of the gas coming from the fibers 40" drops according to the ratio between the gas volume flow in the channel 24" and in the fibers 40".

From the chamber 19", the blended gas stream again flows in parts into channel 24" and in parts into the second bundle of fibers 41". This process is repeated with each chamber and each bundle of fibers until the final gas evacuation chamber 5" is reached, which is in communication with the flexible tube 9". Supplying each chamber 19" with a gaseous mixture that is less rich in carbon dioxide increases the local $CO_2$ concentration gradient between the gas in the fiber, which is at a relative low pressure, and the gas in the blood, which is at a relative high pressure, so that gas exchange is considerably increased.

The flow resistance for the gaseous mixture in the annular channel 24" is substantially the result of the size of the catheter 4" and of the size and shape of the cradle 23". The gas resistance affects the ratio of the gas flowing in the channel 24" and in the bundle of fibers 3". The pressure drop between the chambers 5" and 6" is not influenced by the channel 24" since it substantially depends on the gas resistance in the fibers 3" and because the flow through the fibers 3" is constant. The channel 24" causes an increase in the flow of the overall volume which results in an increased pressure drop in the central catheter 4". Therefore, the channel 24" permits to better evacuate carbon dioxide without causing an increased pressure drop in the fibers 3". Hereto before, this was one of the major problems with intravenous oxygenators. Tests showed that, with the fibers described herein above, flows through the fibers of about 0.5 l/min are advantageous since with these values the pressure drop remains quite low. Pressure drop is proportional to the square of the flow velocity.

More specifically, the ratio between the volume flow in the free channel and the volume flow in the fibers may be greater than 3, preferably greater than 4. Particularly good gas exchange values were achieved with a ratio of about 5.

It should be emphasized that a channel system that supplies the bundles of fibers with a gas less rich in carbon dioxide, more specifically having the volume flow conditions mentioned, by means of a free channel via mixing chambers is advantageous and inventive by itself, irrespective of all of the other proposed features.

As a matter of course, it is also possible to combine features of the exemplary embodiments shown. In another oxygenator, a common gas supply can for example be provided for fibers that extend through the length of the oxygenator and are divided along their length. The length of the various segments may also vary for example.

More specifically, the pump can lie on the side of the oxygenator against which the blood flows first. For this purpose, the impermeable sheath should be sealingly connected to the pump so that the flow from the rotor inlet to the rotor outlet is only allowed via the rotor. Advantageously, an oxygenator constructed in this way can be more easily removed from the vena cava after use because the sheathing simply comes to lie flat against the oxygenator during removal thereof.

Moreover, with an oxygenator that carries the pump in that end of an impermeable sheathing against which the flow is directed, the blood pressure within the sheathing is higher than in the physiological circulation. The resulting force acts radially outward onto the sheathing. This force may be used to expand the sheathing to the diameter required for use.

With the pump unit being located at that end of the oxygenator against which the flow is directed, the object is to dispose the pump, the gas supply means and the gas return means so that they occupy as little space as possible. In order to keep the length of the oxygenator as short as possible, it is advisable to arrange the required components in a cross-section.

For this purpose, a common cartridge is proposed in which a catheter, and preferably the pump as well, are arranged off-center. As a rule, the pump needs a greater cross-section than a gas catheter. With a catheter being disposed in the center of the oxygenator's cross-section and with a pump being located beside the catheter, the radius of the oxygenator there must already be half the diameter of the catheter plus the entire diameter of the pump. With the pump being located in the center and with a catheter extending laterally from the pump, the radius required for the oxygenator is half the diameter of the pump plus the diameter of the catheter. Accordingly, by disposing the catheter off-center, one obtains an advantageous cross-section, given the pump has a larger diameter than the catheter.

The pump unit of the oxygenator can have a particularly space-saving configuration if the catheter and the pump are both disposed off-center in such a manner that the longitudinal axis of the oxygenator lies on a line joining the longitudinal axis of the pump and the longitudinal axis of the catheter. The perimeter of the pump may thereby fit against the perimeter of the oxygenator on the pump unit, for example against the wall of a common cartridge for pump and catheter.

The impermeable sheathing of the oxygenator can be connected directly to a cartridge. A cylindrical cartridge is particularly suited for fastening.

Such an implementation is given in the exemplary embodiment shown in the FIGS. 11 and 12. The oxygenator 100 substantially consists of eight bundles of fibers (labeled at 101, 102 by way of example) that are connected in series and are disposed together with the pump unit 103 in an impermeable sheathing 104.

The bundles of fibers are retained alongside an oxygen catheter 105 on fiber holders (labeled at 106, 107, 108 by way of example) and are guided along together with the latter. Two neighboring fiber holders 106, 108 of different bundles of fibers are connected together so that they are not rotatable relative to each other and cannot be displaced lengthwise by means of a cylindrical sheathing (labeled at 109 by way of example), said sheathing being connected to sweat soldered connections (labeled at 110, 111 by way of example) such as by clamping or gluing. A mixing chamber 112 is formed between the sweat soldered connections 110, 111 and the sheathing 109.

On its inner side, the mixing chamber 112 concurrently communicates with a circular ring mixing channel 113. Without interruption the mixing channel 113 extends from an oxygen feed chamber 114 to a drain connection 115 of a cylinder cartridge 116 between the oxygen catheter 105 and the fiber holders 106, 107, 108. At the drain connection 115, the mixing channel 113 merges into a hollow chamber 117. In the hollow chamber 117, the oxygen catheter 105 and a pump 118 are disposed off-center with the pump 118 fitting directly against a cartridge wall 119 where it is fixed by a separating chamber (not labeled). The separating chamber is sealed against the hollow chamber 117. The only exception is the cable bushing 120. An electric cable 121 extends through said cable bushing 120 from the pump 118 into the hollow chamber 117 and from there together with the oxygen catheter 105 through a flexible tube 122. The hollow chamber 117 is connected to the flexible tube 122. The pump 118 however is configured to be substantially conical on its side facing the cable bushing 120, providing by itself a seal for the bushing 120. The cartridge 116 is coaxial with the longitudinal axis of the oxygenator 100 and is divided in two parts except for a connection 124 of the hollow chamber 117 for recirculating carbon dioxide enriched gas so that a pump inlet 125 is free for the blood to flow toward it.

Neighboring fiber holders 106, 107 of the same bundle of fibers are rotated 240° relative to one another. The bundles of fibers consisting of fibers of 35 mm in length are twisted accordingly (in each bundle, one fiber is indicated and labeled by way of example at 130). The fiber holders are adjacent so as to provide a form-positive fit and comprise at the annular abutting surface respectively a groove 131 and a lug 132 so that they are prevented from untwisting as long as they are not moved apart to such an extent that the groove allows the lug to come free. Inside the bundles of fibers, the fiber holders 106, 107 are additionally connected to an elastic membrane (labeled at 133 by way of example). The membrane 133 seals the mixing channel 113 against the flow space provided for the blood between the fiber holders 106, 107, 108 and the sheathing of the oxygenator 100. At that end of the oxygenator 100 against which the flow is directed the sheathing 104 is sealingly connected to the cartridge 116 so that on this side inflow of blood is only allowed through the pump inlet 125.

When the oxygenator 100 is operating, the pump 118 generates excess pressure within the sheathing 104. The gas pressure must always be lower than the blood pressure so that, when the blood pressure is increased, the gas pressure can be also increased accordingly. Tests showed that this provision alone already yields a gas exchange increased by one tenth.

By disposing the pump unit 103 at the end against which the flow is directed, it is additionally possible to have the downstream end of the sheathing 104 implemented without fastening means. The blood pressure automatically causes the sheathing 104 to expand in the radial direction and the blood flow direction causes it to stretch in the longitudinal direction. As a result of the simple structure of the sheathing, the oxygenator can be more readily removed after its utilization in the vena cava.

The invention claimed is:

1. An intravenous oxygenator for insertion into a vein having a bundle of fibers allowing through flow of oxygen and carbon dioxide therealong, said fibers being each connected to a gas supply means through a first connection and to a gas evacuation means through a second connection so that oxygen and carbon dioxide are allowed to flow through the fibers from the first connections to the second connections, said connections being respectively connected to a first and to a second fiber holder and being displaceable along a longitudinal axis of the oxygenator,
   wherein the fiber holders are sliding bodies that are rotatable relative to one another about the longitudinal axis of the oxygenator, more specifically relative to the central catheter, and that are mounted so as to be displaceable preferably along said axis;
   the oxygenation comprising a housing with an impermeable sheathing that is deformable in the radial direction in particular; and
   further comprising a wire grate used as the carrier structure of the housing.

2. The intravenous oxygenator as set forth in claim 1, comprising a first driver provided on the first fiber holder and a second driver provided on the second fiber holder, said drivers being directed toward each other and allowing rotation of the first fiber holder relative to the second fiber holder at least in one direction of rotation up to a rotation limit only without the second fiber holder being carried along when the two fiber holders are pressed into contact with each other.

3. The intravenous oxygenator as set forth in claim 2,
   wherein the rotation limit is a relative rotation of from 90° to 300°, for each 30 mm fiber length between the two fiber holders.

4. The intravenous oxygenator as set forth in claim 3,
   wherein the rotation limit is a relative rotation of from 150° to 270° for each 30 mm fiber length between the two fiber holders.

5. The intravenous oxygenator as set forth in claim 4,
   wherein the rotation limit is a relative rotation of about 240°, for each 30 mm fiber length between the two fiber holders.

6. The intravenous oxygenator as set forth in claim 1,
   comprising an abutment device provided on fiber holders for limiting a displacement of the connections relative to one another.

7. The intravenous oxygenator as set forth in claim 1,
   wherein fiber holders are disposed in the inner volume of the bundle of fibers.

8. The intravenous oxygenator as set forth in claim 1, comprising a substantially elastic bond between two fiber holders.

9. The intravenous oxygenator as set forth in claim 8, wherein the elastic bond comprises a membrane and/or a linear spring.

10. The intravenous oxygenator as set forth in claim 1, comprising a spiral guidance means for guiding fiber holders along the longitudinal axis of the oxygenator.

11. The intravenous oxygenator as set forth in claim 1, comprising a blood pump for pumping blood through the bundle of fibers.

12. The intravenous oxygenator as set forth in claim 1, wherein when the bundle of fibers is twisted, there is equilibrium of moments between the fibers and the force-transmitting bonds between the connections.

13. The intravenous oxygenator as set forth in claim 12, wherein it is assumed that the equilibrium of moments is achieved with a relative rotation of from 90° to 300°, for each 30 mm fiber length between the two fiber holders.

14. The intravenous oxygenator as set forth in claim 13, wherein it is assumed that the equilibrium of moments is achieved with a relative rotation of from 150° to 270°, for each 30 mm fiber length between the two fiber holders.

15. The intravenous oxygenator as set forth in claim 14, wherein it is assumed that the equilibrium of moments is achieved with a relative rotation of about 240°, for each 30 mm fiber length between the two fiber holders.

16. The intravenous oxygenator as set forth in claim 1, wherein the housing can expand to a diameter of 30 mm at the most.

17. The intravenous oxygenator as set forth in claim 16, wherein the housing can expand to a diameter of 25 mm at the most.

18. An intravenous oxygenator for insertion into a vein having a bundle of fibers allowing through flow of oxygen and carbon dioxide therealong, said fibers being each connected to a gas supply means through a first connection and to a as evacuation means through a second connection so that oxygen and carbon dioxide are allowed to flow through the fibers from the first connections to the second connections, said connections being respectively connected to a first and to a second fiber holder and being displaceable along a longitudinal axis of the oxygenator,
wherein the fiber holders are sliding bodies that are rotatable relative to one another about the longitudinal axis the oxygenator, more specifically relative to the central catheter, and that are mounted so as to be displaceable preferably along said axis; and
the oxygenator further comprising a gear connected to a bundle of fibers.

19. The intravenous oxygenator as set forth in claim 18, wherein on a rotation device for twisting a plurality of fiber bundles connected in series, a gear is provided between the rotation device and a bundle of fibers in such a manner that the gear transmits a rotation of the rotation device onto the bundles of fibers at a ratio corresponding to the number of fiber bundles or to a ratio of the overall length of the bundles of fibers to a scale length.

* * * * *